United States Patent
Yao et al.

(10) Patent No.: US 7,627,202 B2
(45) Date of Patent: Dec. 1, 2009

(54) METHOD FOR MANUFACTURING OPTICAL FIBER PROBE

(75) Inventors: Yuan Yao, Beijing (CN); Shou-Shan Fan, Beijing (CN)

(73) Assignees: Tsinghua University, Beijing (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 0 days.

(21) Appl. No.: 11/829,862

(22) Filed: Jul. 27, 2007

(65) Prior Publication Data

US 2008/0025663 A1    Jan. 31, 2008

(30) Foreign Application Priority Data

Jul. 28, 2006    (CN) .................... 2006 1 0061853

(51) Int. Cl.
*G02B 6/00* (2006.01)
*G02B 6/26* (2006.01)
*G02B 6/42* (2006.01)

(52) U.S. Cl. .................. 385/12; 65/429; 65/431; 216/7; 385/43

(58) Field of Classification Search .......... 385/12, 385/13, 43; 65/385, 403, 429–431; 216/7
See application file for complete search history.

(56) References Cited

U.S. PATENT DOCUMENTS 5,288,999 A * 2/1994 Betzig et al. .......... 250/227.26
5,664,036 A * 9/1997 Islam .................... 385/31
5,812,723 A * 9/1998 Ohtsu et al. ............ 385/128
5,908,562 A * 6/1999 Ohtsu et al. ............ 216/11
6,236,783 B1 * 5/2001 Mononobe et al. ...... 385/43

FOREIGN PATENT DOCUMENTS

| CN | 1805061 A | | 7/2006 |
| JP | 59053804 A | * | 3/1984 |
| JP | 11-83872 A | | 3/1999 |
| JP | 2000-266655 A | | 9/2000 |
| JP | 2005-17307 A | | 1/2005 |
| WO | WO2006005111 A1 | | 1/2006 |

OTHER PUBLICATIONS

Guo-Ping Zhang, et al., Manufacture and Analysis of the Optic Fiber Probe in Scanning Near-Field Optical Microscope, Opto-Electronic Engineering, Apr. 30, 1999, vol. 26 (2), p. 20-24, China, Abstract.
Ewan Polwart, et al., Novel SERS-Active Optical Fibers Prepared by the Immobilization of Silver Colloioal Particles, Applied Spectroscopy, Nov. 4, 2000, vol. 54 (4), p. 522-527.
Xu Wei-Qing, et al., Studies on the SERS-Active Optic Fiber Probe, Chemical Journal of Chinese Universities, Jan. 31, 2004, vol. 25(1), p. 144-147, China.

* cited by examiner

*Primary Examiner*—Daniel Petkovsek
(74) *Attorney, Agent, or Firm*—Wei Te Chung

(57) ABSTRACT

A method for manufacturing an optical fiber probe includes the steps of providing an optical fiber including a core and a outer protective layer disposed therearound; removing a portion of the outer protective layer to expose a portion of the core; etching the exposed portion of the core to achieve a predetermined shape and thus form a detector; surrounding the detector with a gel solution containing metal particles; and evaporating a solvent in the gel solution to form a metal layer on the surface of the detector.

14 Claims, 5 Drawing Sheets

METHOD FOR MANUFACTURING OPTICAL FIBER PROBE

BACKGROUND OF THE INVENTION

1. Field of the Invention

The invention relates to methods for manufacturing optical fiber probes and, particularly, to a method for manufacturing an optical fiber probe used to detect Raman signal.

2. Description of Related Art

The surface Raman spectrum plays an important role in diverse fields including surface-behavior science and materials science. More particular, surface-enhanced Raman scattering (SERS), in which the Raman spectrum intensity is found to be greatly enhanced, is observed for a large number of molecules adsorbed on the surfaces of metals. The Raman spectrum intensity enhancement can be up to 14 orders of magnitude so that the SERS technique has the merit of great sensitivity. Many mechanisms have been proposed over the past twenty years to account for the enhancement of the Raman spectrum intensity. With the development of high-resolution confocal Raman microscopy, great achievement has been made in development of the SERS technique. In addition, it is believed that the possibility of obtaining the surface-enhanced Raman spectrum of a single molecule would constitute a breakthrough progress in this area. For example, using such an SERS technique, it may then be possible to detect, e.g., a single molecule adsorbed on the surface of a single nano-scale silver particle. The results therefrom could potentially show extraordinarily high Raman spectrum intensity ($10^{14}$ or so) and obtain the Raman spectrum with higher quality. Thus, the SERS technique is thought to be an important research tool for molecular science. Due to the high sensitivity of the SERS technique, it is also considered that the SERS technique is promising in the respect that it might be extensively used to detect the trace molecules in a solution or gas.

Using an optical fiber to detect a Raman signal allows the SERS technique to be employed, in practice. Referring to FIG. 4, a conventional optical fiber probe system 30 includes an optical fiber probe 32 and a spectrum analysis device 36. The optical fiber probe 32 has a first end 322 and an opposite second end 324. A metal thin film or metal particles is/are coated on the surface of the first end 322. Molecules adsorbed on the metal thin film or on the metal particles will generate intense SERS by illumination from an outer laser 34. The optical signals of the SERS are transmitted from the first end 322 of the optical fiber 32 to the second end 324 of the optical fiber 32. Then, the optical signals are received by the spectrum analysis device 36 from the second end 324 and then are analyzed. In such case, it is realized that the optical fiber probe 32 mentioned above is easily inserted into a sample 38 to be measured, instead of putting the sample 38 on a specific platform of a detection device. That is, the detection efficiency can be improved, and the optical fiber probe system 30, as a whole, can be fairly compact.

Additionally, referring to FIG. 5, another conventional optical fiber probe system 40 includes a single optical fiber probe 42, through which an activating light emitted from a light source 44 and a Raman scattering light from a surface of a specimen 48 both can travel together. The activating light emitted from a light source 44 is reflected, in turn, by a half mirror 442 and a reflective mirror 444 and subsequently focused by a focusing lens 46. The focused light enters the single optical fiber probe 42 from a second end 424 thereof and is transmitted through the single optical fiber probe 42 and emitted from a first end 422, so as to irradiate a sample 48.

Then, the Raman scattering light produced from the surface of the sample 48 enters the single optical fiber probe 42 from the first end 422 and transmits to the second end 424. A spectrum analysis device 52 detects the light returning from the surface of the sample 48 in the light path of passing through the focusing lens 46, reflective lens 444, and half mirror 442, sequentially. In such case, the optical fiber probe system 40 mentioned above is favored for miniaturization because the activating light and the Raman scattering light use the same light path.

As mentioned above, the first ends 322, 422 of the optical fiber probe 33, 42 serving as detectors are generally coated with metal particles or the thin film by evaporation, electroplating, or sputtering. These methods are necessarily performed in a vacuum chamber or in an electrolyte. In addition, a heat treatment for the optical fiber is required to increase the adhesion quality and the roughness of the metal particles or the thin film.

What is needed, therefore, is a method for manufacturing an optical fiber probe that is easier and that has no requirement for additional vacuum device and heat treatment process.

SUMMARY OF THE INVENTION

A method for manufacturing an optical fiber probe is provided. In one present embodiment, the method includes the steps of: providing an optical fiber including a core and an outer protective layer disposed therearound; removing a portion of the outer protective layer to expose a portion of the core; etching the exposed portion of the core to achieve a predetermined shape to form a detector; surrounding the detector with a gel solution containing metal particles; and evaporating a solvent in the gel solution to form a metal layer on the surface of the detector.

Other advantages and novel features of the present method for manufacturing an optical fiber probe will become more apparent from the following detailed description of preferred embodiments when taken in conjunction with the accompanying drawings.

BRIEF DESCRIPTION OF THE DRAWINGS

Many aspects of the present method for manufacturing an optical fiber probe can be better understood with reference to the following drawings. The components in the drawings are not necessarily to scale, the emphasis instead being placed upon clearly illustrating the principles of the present method for manufacturing an optical fiber probe.

Figure 1:
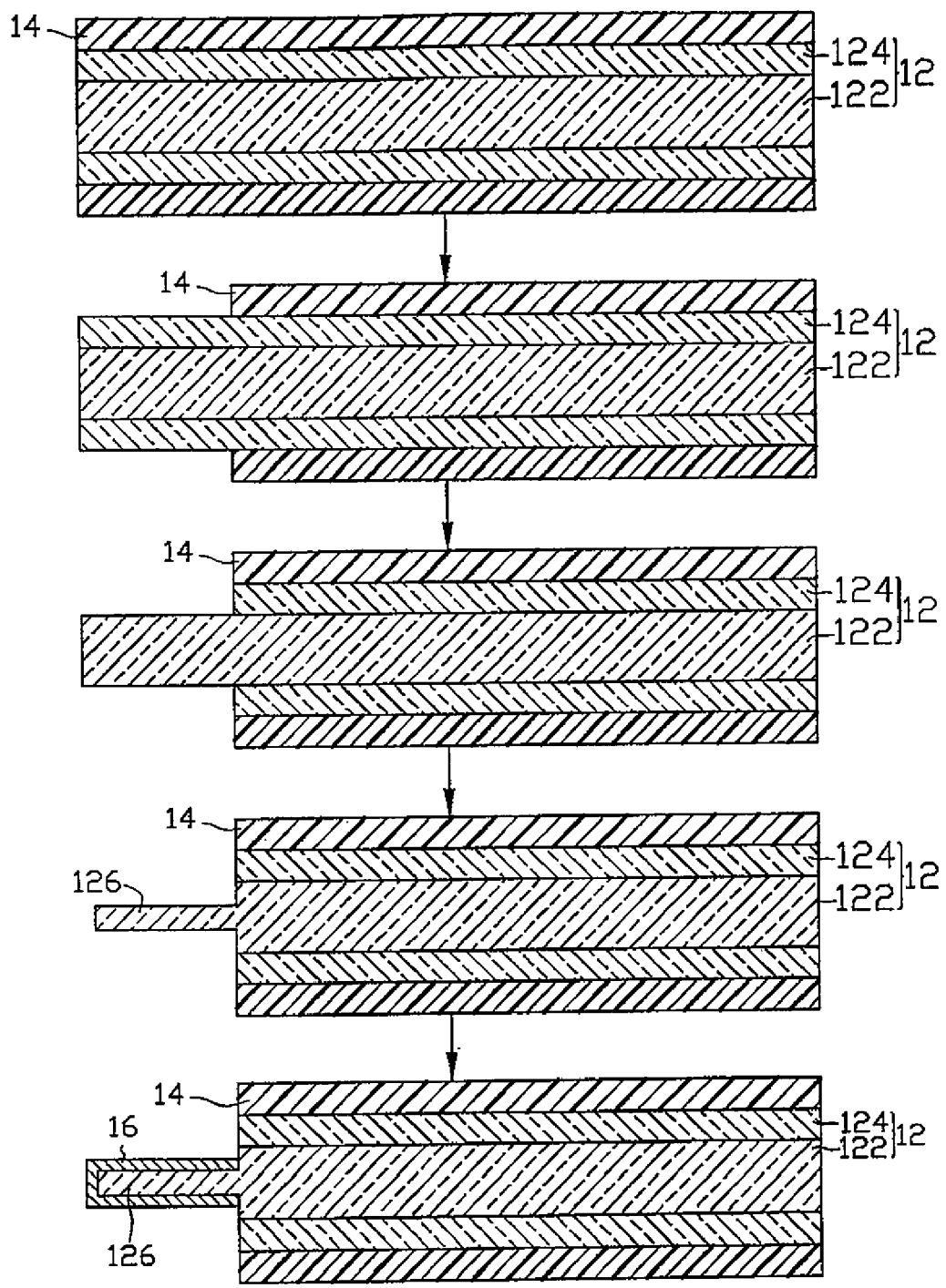
FIG. 1 is a flowchart showing a method for manufacturing an optical fiber probe, in accordance with a present embodiment.

Corresponding reference characters indicate corresponding parts throughout the several views. The exemplifications set out herein illustrate at least one preferred embodiment of the present method for manufacturing optical fiber probe, in one form, and such exemplifications are not to be construed as limiting the scope of the invention in any manner.

DETAILED DESCRIPTION OF THE INVENTION

Reference will now be made to the drawings to describe embodiments of the present method for manufacturing an optical fiber probe, in detail.

Referring to FIG. 1, a method for manufacturing an optical fiber probe 10, according to a present embodiment, is shown. The method includes the following steps:

(a): providing an optical fiber, which includes a core and an outer protective layer disposed therearound;

(b): removing a portion of the outer protective layer to expose a portion of the core;

(c): etching the exposed portion of the core to arrive at a predetermined shape and thereby form a detector;

(d): surrounding the detector with a gel solution containing metal particles; and (e): evaporating a solvent in the gel solution to form a metal layer on the surface of the detector.

Step (a) provides the optical fiber including the core 12 inside and the outer protective layer 14 outside. That is, the core 12 is surrounded by the outer protective layer 14 and is in contact therewith. The core 12 and the outer protective layer 14 are coaxially disposed to each other.

In the present embodiment, the optical fiber can be a single-mode optical fiber or a multi-mode optical fiber. The outer protective layer 14 can be made of plastic or resin. The core 12 further includes an inner core 122 and an outer core 124 that are coaxially disposed adjacent to each other. The inner core 122 and/or the outer core 124 can, beneficially, be made of a quartz glass. In addition, a refractive index of the outer core 124 is lower than a refractive index of the inner core 122, in order to promote total internal reflection.

Step (b) removes the portion of the outer protective layer 14 to expose the portion of the core 12, which is configured to detect a given Raman signal. In particular, the portion of the outer protective layer 14 at one end of the optical fiber is stripped/etched off so that the portion of the core 12 corresponding to the removed outer protective layer 14 is exposed.

In Step (c), the exposed portion of the core 12 is controllably etched by dipping it into an acid solution to form the detector 126. In particular, the outer core 124 of the core 12 is etched firstly and the inner core 122 is etched by the advance by the acid solution. As a result, the detector 126 with the predetermined shape is formed. In such case, the inner core 126 is etched in a cylinder shape, as shown in FIG. 1.

The acid solution can, advantageously, be hydrofluoric (HF) acid or amino fluoride acid. However, other solutions having a capacity to chemically etch the core 12 of the optical fiber also can be employed. The shape of the detector 126 can be controlled, e.g., by a dipping time in the acid solution and by the strength of the acid employed. For example, the cylinder shape can be formed by etching it for a shorter time, while a cone shape can be formed by etching it for a longer time.

In addition, after the step (c), the method in the present embodiment can further include the following step of dipping the detector 126 into an alkaline solution. This step is used to remove and/or neutralize any acid solution remaining on the surface of the detector 126 and to form a negative ion layer on the surface of the detector 126. In the present embodiment, the alkaline solution can, usefully, include at least one alkaline material selected from the group consisting of sodium hydroxide (NaOH), potassium hydroxide (KOH), calcium hydroxide (CaOH), sodium carbonate ($Na_2CO_3$), potassium carbonate ($K_2CO_3$), calcium carbonate ($CaCO_3$), sodium hydrogen carbonate ($NaHCO_3$), potassium hydrogen carbonate ($KHCO_3$), and calcium hydrogen carbonate ($Ca(HCO_3)_2$).

Step (d) surrounds the detector 126 with the gel solution containing metal particles (i.e., metal-carrying gel). In this step, the detector 126 can be dipped into the metal-carrying gel. In particular, the gel solution beneficially contains nano-scale metal particles dissolved in a solvent. The solvent can e.g., be a nonpolar solution, such as cyclohexylamine or chloroform. A readily available source of metal particles is metal powder. The nano-scale metal particles can, advantageously, be selected from the group consisting of gold (Au), silver (Ag), copper (Cu), and platinum (Pt), as well as alloys of such metals. Gold (Au), silver (Ag), copper (Cu), and platinum (Pt), as noble metals, are known for their high conductivity and chemical durability. Rather opportunely, the gel solution contains gold metal particles. The gold-carrying gel carries positive electric charges, while the surface of the detector 126, on which the negative ion layer is formed, carries negative electric charges. Therefore, when the detector 126 is dipped into the gel solution, the gel solution will be adsorbed on the surface of the detector 126 because the positive electrical charges and the negative electrical charges are mutually attractive. However, the metal-carrying gel is not limited to use of those metals and alloys mentioned above to surround the detector 126. Alternatively, in order to increase the adhesion of to metal particles, the metal-carrying gel could be dropped on the surface of the detector 126.

Step (e) is provided to perform the evaporation of the solvent in the gel solution. In this step, the solvent in the gel solution is evaporated to allow the metal particles, such as the gold metal particles, to adhere on the surface of the detector 126 and finally form a metal layer 16 thereon. In the present embodiment, the metal layer 16 has a thickness of less than 1 μm. Quite usefully, the thickness of the metal layer 16 is in an approximate range from 1 nm to 100 nm.

As mentioned above, the metal particles in the gel solution also can carry natural electrical charges. In such case, the gel solution is dropped directly on the surface of the detector 126, so as to form the metal layer 16 after the solvent of the gel solution is evaporated.

Therefore, because the method for manufacturing the optical fiber probe in the present embodiment does not need a heating device and/or a vacuum chamber to achieve the desired result. Accordingly, it makes manufacturing thereof easier to achieve, and, as such, it is simpler to equip devices in this manner. Therefore, the method of the present embodiment should prove favorable in practice.

Figure 2:
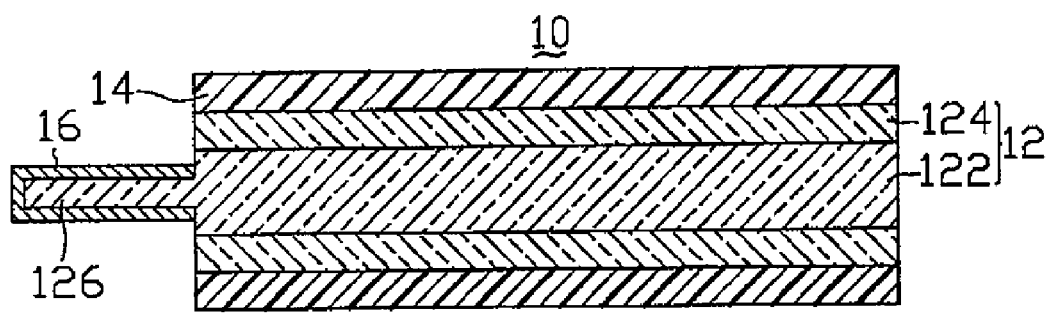
FIG. 2 is a schematic view showing an optical fiber probe formed using the method illustrated in FIG. 1.

In addition, referring to FIG. 2, an optical fiber probe 10, manufactured by the method according to the present embodiment, is shown. The optical fiber probe 10 includes a core 12 and an outer protective layer 14 disposed directly on the core 12. In particular, the outer protective layer 14 and the core 12 are coaxially disposed relative to each other.

The core 12 includes an inner core 122 and an outer core 124. A portion of the inner core 122 extends from one end of the optical fiber probe 10 to serve as a detector 126. A metal layer 16 is formed on the surface of the detector 126. The core 12 is used to transmit the optical signal and collect the Raman signal. The outer protective layer 14 is used to protect the core 12 and to increase the structure strength of the optical fiber probe 10. Moreover, the outer protective layer 14 is also used to cause light constraint (i.e., to promote internal reflection) in the core 12.

In the present embodiment, the inner core 122 and/or the outer core 124 is, advantageously, made of a quartz glass. The respective compositions of the inner core 122 and the outer core 124 are chosen such that a refraction index of the outer core 124 is lower than a refraction index of the inner core 122. Therefore, when light transmitted in the inner core 122 strikes the boundary between the inner core 122 and the outer core 124 at an angle larger than the critical angle, total internal reflection occurs to allow light to travel continuously in the inner core 122.

In the present embodiment, the detector 126 has a cylinder shape. The diameter of the detector 126 is smaller than or equal to the diameter of the inner core 122 of the core 12. Because the characteristics of the metal layer 16 and the protective layer 14 are the same as those mentioned above, the detail description thereof is omitted here for conciseness.

Figure 3:
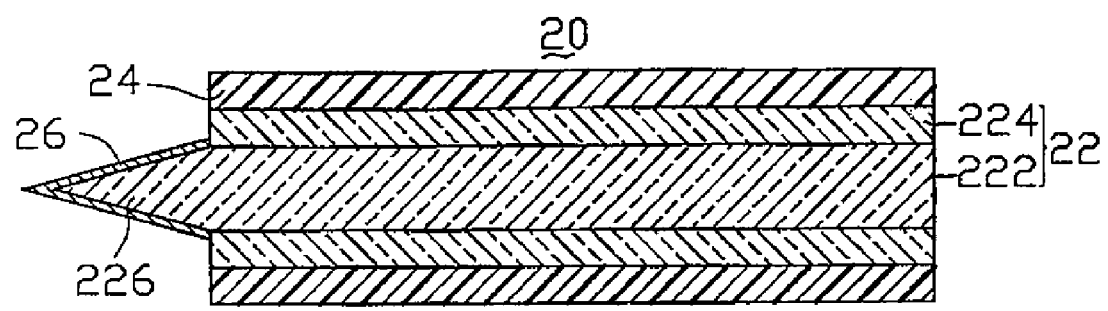
FIG. 3 is a schematic view showing another optical fiber probe formed using the method of FIG. 1.
Figure 4:
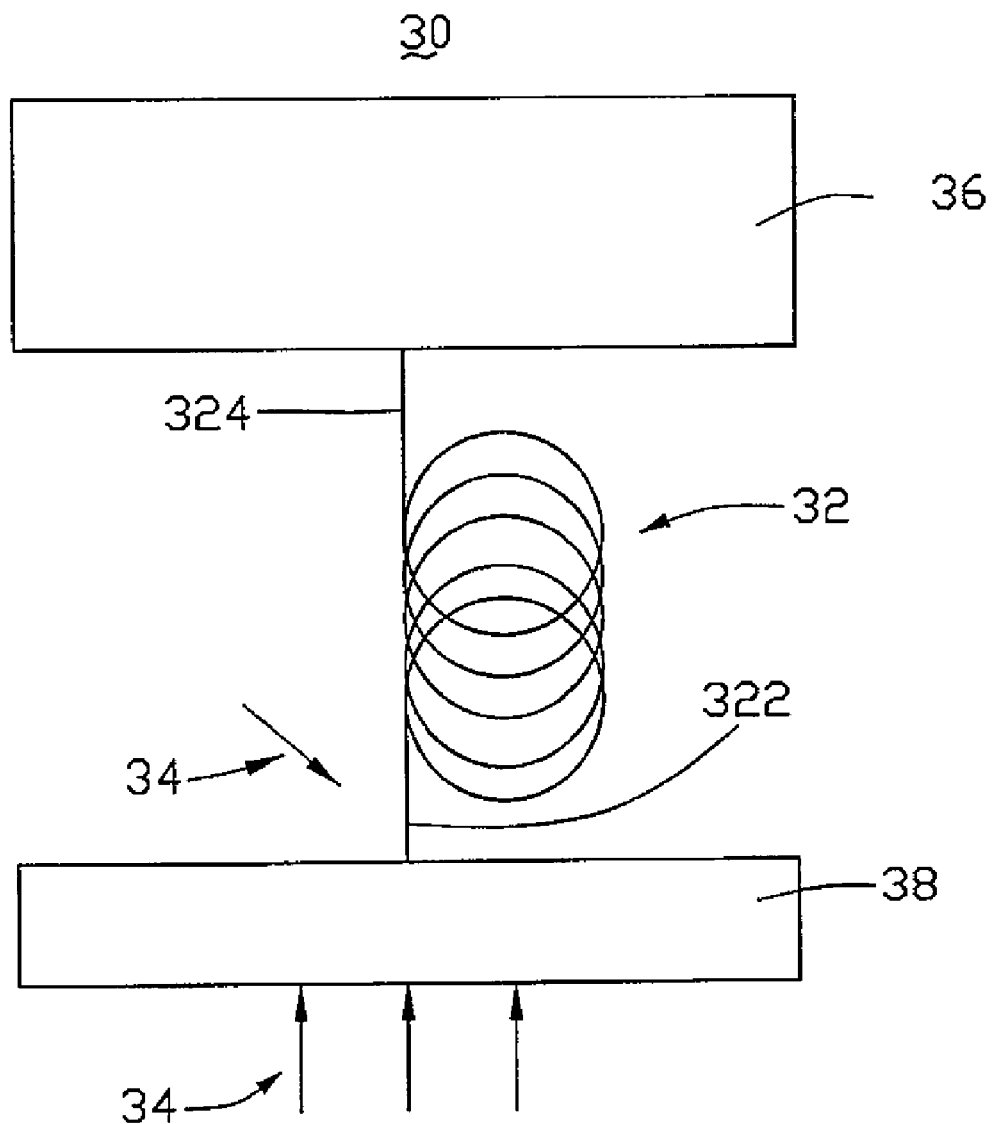
FIG. 4 is a schematic view showing a conventional optical fiber probe system.
Figure 5:
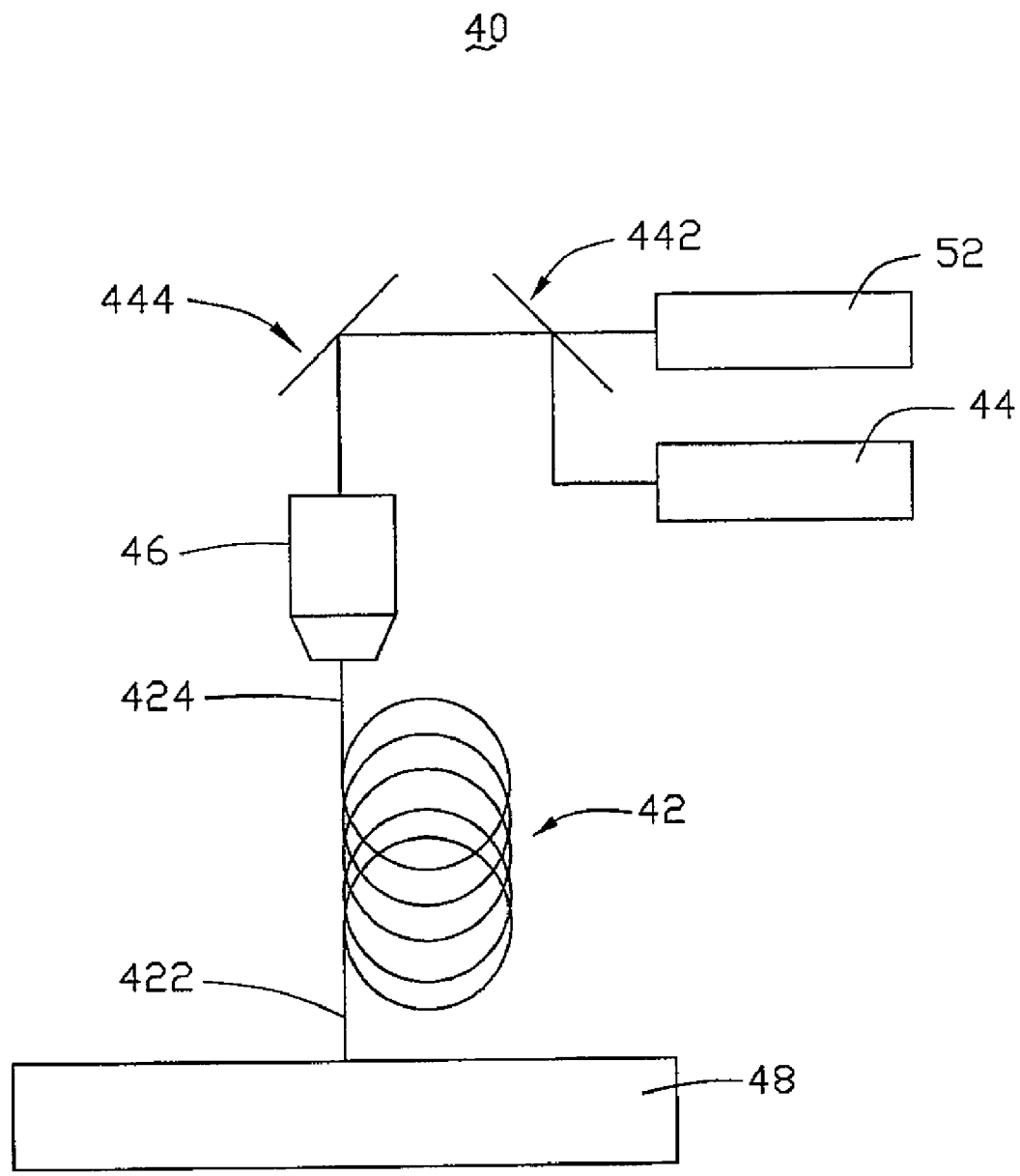
FIG. 5 is a schematic view showing another conventional optical fiber probe system.

Referring to FIG. 3, another optical fiber probe 20, manufactured by the method according to the present embodiment, is shown. The optical fiber probe 20 includes a core 22 and an outer protective layer 24 disposed directly on the core 22. In particular, the outer protective layer 24 and the core 22 are coaxially disposed relative to each other. The core 22 includes an inner core 222 and an outer core 224. A portion of the inner core 222 extends from one end of the optical fiber probe 20 to serve as a detector 226. A metal layer 26 is formed on the surface of the detector 226. The elements and characteristics of the optical fiber probe 20 in the present embodiment are the same as the optical fiber probe 10 mentioned above except with respect to the shape of the detector 226. Specifically, for the optical fiber probe 20, the detector 226 is cone-shaped. However, within the purview of one skilled in the art, the structure/shape of the detector need not be limited just to the cylinder shape or the cone shape. With respect the etching step employed, it is to be understood that any various forms of etching, including chemical/mechanical polishing, chemical etching, plasma etching, etc., could be used and be considered within the scope of the present method.

Finally, it is to be understood that the above-described embodiments are intended to illustrate rather than limit the invention. Variations may be made to the embodiments without departing from the spirit of the invention as claimed. The above-described embodiments illustrate the scope of the invention but do not restrict the scope of the invention.

What is claimed is:

1. A method for manufacturing an optical fiber probe, comprising steps of:
providing an optical fiber comprising a core and an outer protective layer disposed therearound;
removing a portion of the outer protective layer to expose a portion of the core;
etching the exposed portion of the core to yield a predetermined shape and thereby form a detector;
dipping the detector into an alkaline solution to form a negative ion layer on a surface of the detector;
after forming the negative ion layer, surrounding the detector with a gel solution comprising of metal particles and carrying positive electric charges such that the positive electric charges of the gel solution can be attracted by the negative ions of the negative ion layer thereby the gel solution being adsorbed on the surface of the detector; and
evaporating a solvent in the gel solution to form a metal layer on the surface of the detector.

2. The method as claimed in claim 1, wherein the exposed portion of the core is etched by dipping thereof into an acid solution.

3. The method as claimed in claim 2, wherein the acid solution is hydrofluoric acid or amino fluoride acid.

4. The method as claimed in claim 1, wherein the detector is dipped into the gel solution in order to surround the detector therewith.

5. The method as claimed in claim 1, wherein the gel solution is applied to the surface of the detector in order to surround the detector therewith.

6. The method as claimed in claim 1, wherein the alkaline solution is comprised of at least one alkaline material selected from the group consisting of sodium hydroxide, potassium hydroxide, calcium hydroxide, sodium carbonate, potassium carbonate, calcium carbonate, sodium hydrogen carbonate, potassium hydrogen carbonate and calcium hydrogen carbonate.

7. The method as claimed in claim 1, wherein the metal layer is comprised of at least one of gold, silver, copper, and platinum.

8. The method as claimed in claim 1, wherein a thickness of the metal layer is in an approximate range from 1 nm to 100 nm.

9. The method as claimed in claim 1, wherein the predetermined shape is a cylinder or a cone.

10. The method as claimed in claim 1, wherein the metal particles is selected from the group consisting of gold, silver, copper, platinum, and alloys thereof.

11. The method as claimed in claim 1, wherein after evaporation, the metal particles are adhered on the surface of the detector.

12. The method as claimed in claim 1, wherein the metal particles are in nano-scale.

13. A method for manufacturing an optical fiber probe, comprising steps of:
providing an optical fiber comprising a core and an outer protective layer disposed therearound;
removing a portion of the outer protective layer to expose a portion of the core;
etching the exposed portion of the core to yield a predetermined shape thereby form a detector;
applying an alkaline solution to the detector to form a negative ion layer on a surface of the detector;
after forming the negative ion layer, surrounding the surface of the detector with a gel solution containing metal particles and carrying positive electric charges such that the positive electric charges of the gel solution can be attracted by the negative ions of the negative ion layer thereby the gel solution being adsorbed on the surface of the detector; and
evaporating a solvent in the gel solution to form a metal layer on the surface of the detector.

14. The method as claimed in claim 13, wherein the exposed portion of the core is etched by an acid solution.

* * * * *